(12) United States Patent
Pajunk et al.

(10) Patent No.: US 7,074,208 B2
(45) Date of Patent: Jul. 11, 2006

(54) DEVICE FOR FIXATION OF CATHETER AND FILTER

(75) Inventors: Heinrich Pajunk, Geisingen (DE); Horst Pajunk, Geisingen (DE)

(73) Assignee: Gebruder Pajunk Besitzverwaltung OHG (DE)

( * ) Notice: Subject to any disclaimer, the term of this patent is extended or adjusted under 35 U.S.C. 154(b) by 151 days.

(21) Appl. No.: 10/716,281

(22) Filed: Nov. 18, 2003

(65) Prior Publication Data

US 2005/0107746 A1    May 19, 2005

(51) Int. Cl.
*A61M 5/32*    (2006.01)
(52) U.S. Cl. .................... 604/180; 128/DIG. 6
(58) Field of Classification Search .......... 604/174, 604/180, 179; 128/912, DIG. 6, DIG. 26
See application file for complete search history.

(56) References Cited

U.S. PATENT DOCUMENTS

| | | | | |
|---|---|---|---|---|
| 3,568,679 A | * | 3/1971 | Reif | 604/180 |
| 4,419,094 A | * | 12/1983 | Patel | 604/165.01 |
| 4,561,857 A | | 12/1985 | Sacks | |
| 4,711,636 A | * | 12/1987 | Bierman | 604/180 |
| 5,354,282 A | * | 10/1994 | Bierman | 604/180 |
| 5,389,082 A | * | 2/1995 | Baugues et al. | 604/174 |
| 5,944,696 A | * | 8/1999 | Bayless et al. | 604/174 |
| 6,428,514 B1 | | 8/2002 | Goebel | |

FOREIGN PATENT DOCUMENTS

| | | |
|---|---|---|
| EP | 0 972 537 A2 | 1/2000 |
| FR | 2 351 348 A | 12/1977 |
| GB | 0972537 A2 * | 1/2000 |

* cited by examiner

*Primary Examiner*—Catherine S. Williams
(74) *Attorney, Agent, or Firm*—Akerman Senterfitt; Stephan A. Pendorf

(57) ABSTRACT

The invention concerns a device for anchoring a filter (50) and a catheter (40), comprising an adhesive bandage (10), a securing element (20) for anchoring the catheter (40) and a carrier element (30) for anchoring the filter (50), wherein either the securing element (20) or the carrier element (30) is applied to the adhesive bandage (10), and wherein the securing element (20) includes a first coupling element, which is releaseably connectable with a second coupling element provided on the carrier element (30).

12 Claims, 3 Drawing Sheets

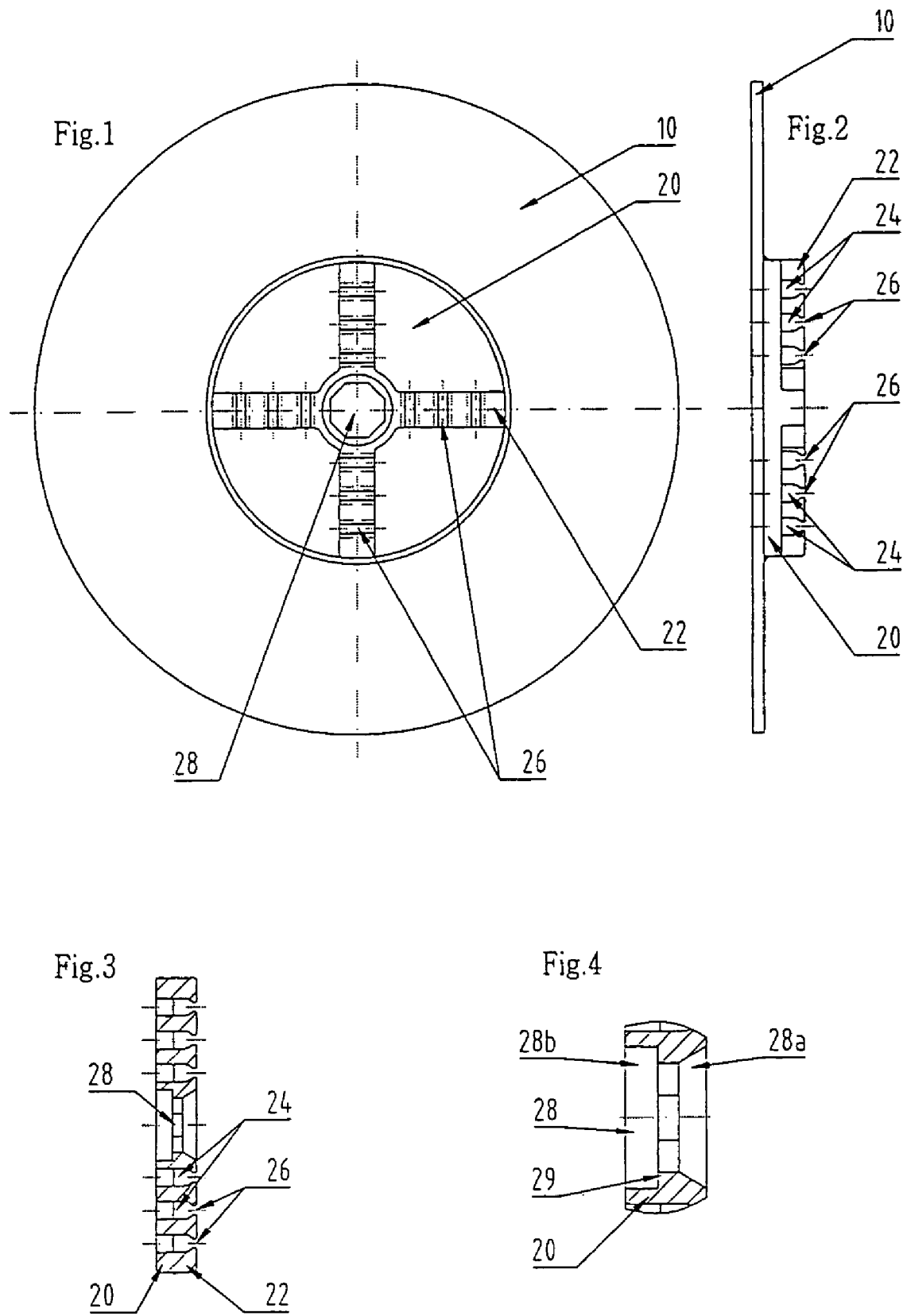

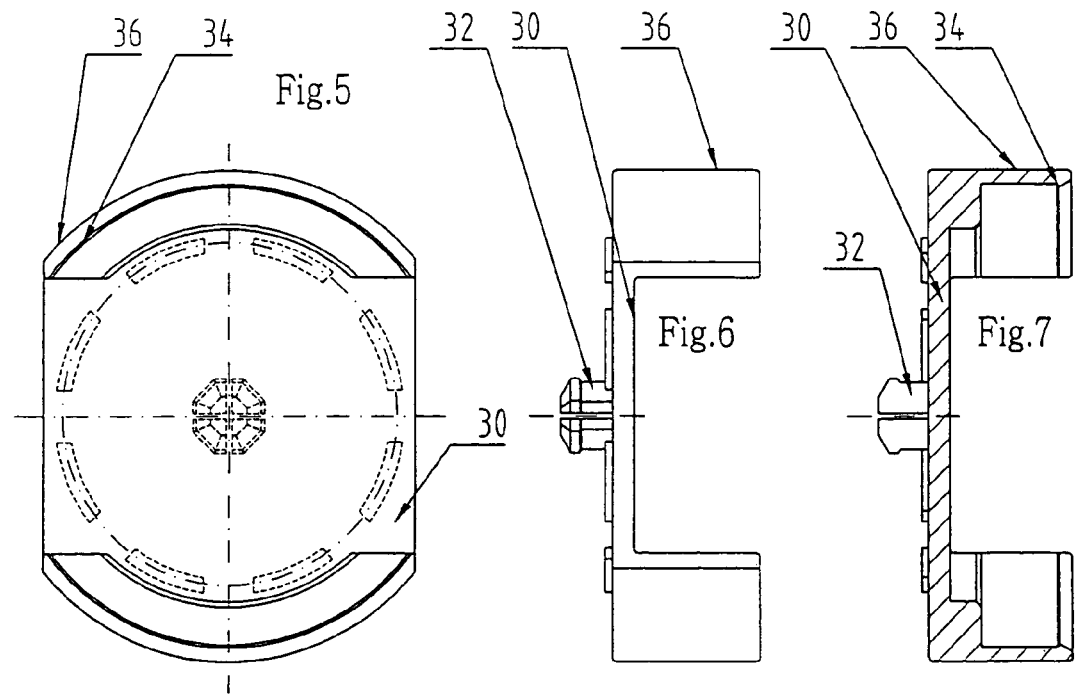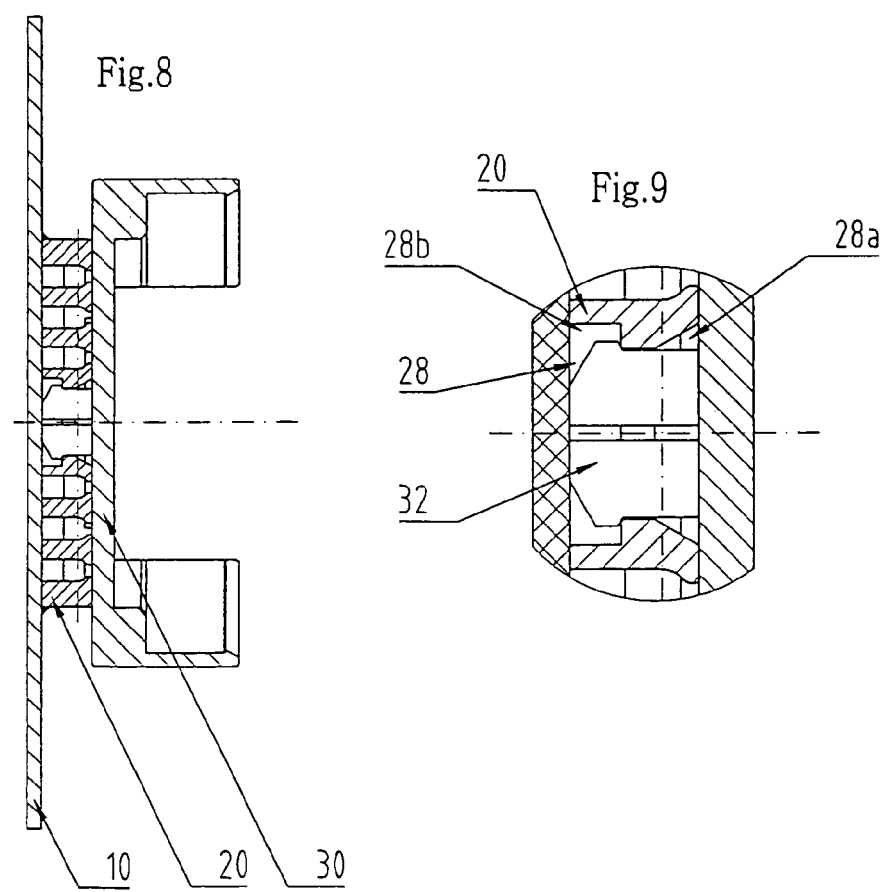

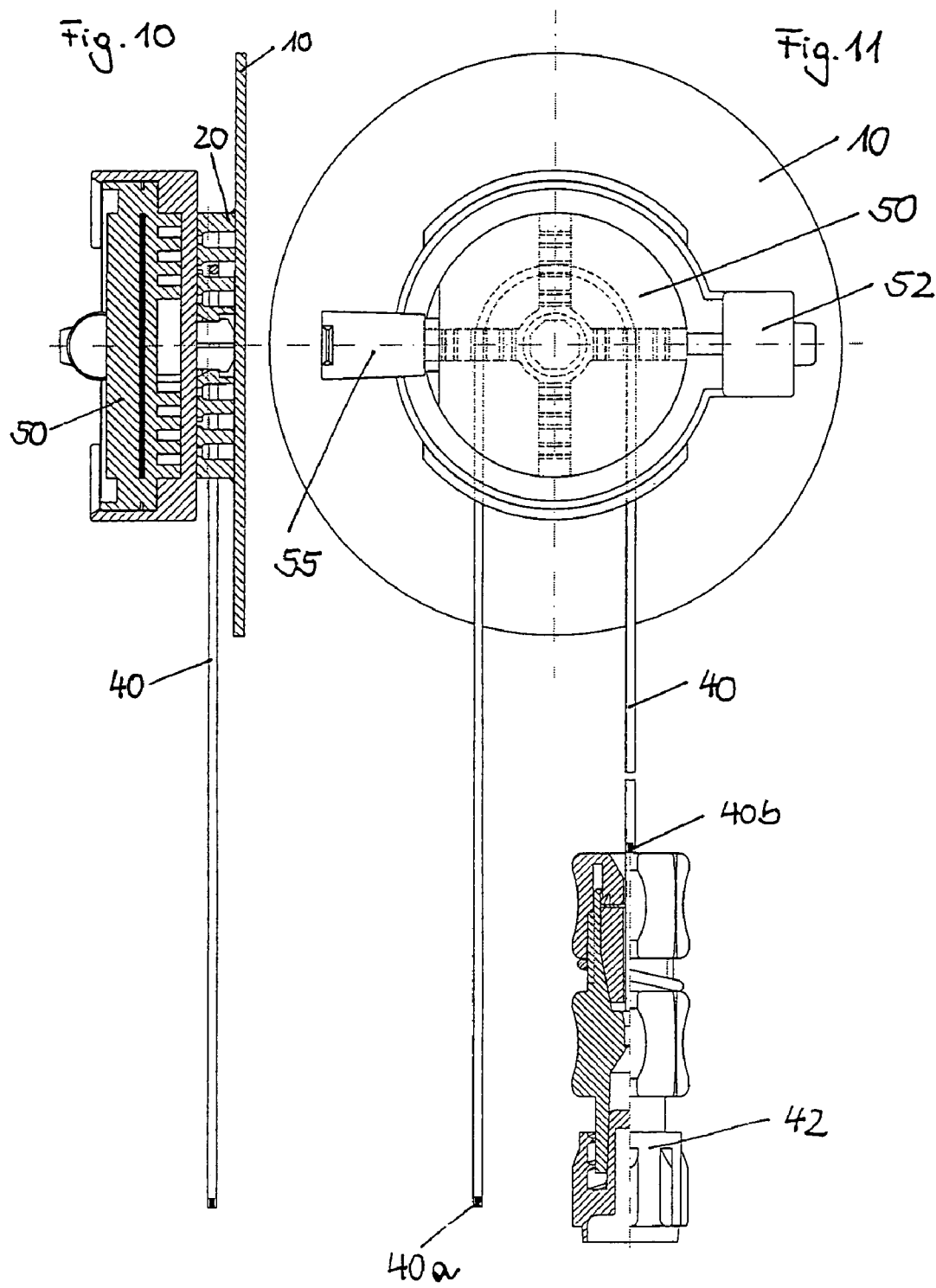

DEVICE FOR FIXATION OF CATHETER AND FILTER

BACKGROUND OF THE INVENTION

1. Field of the Invention

The invention concerns a device for fixation of catheter and filter.

2. Description of the Related Art

If a catheter is introduced into a patient, for example for administration of an anesthetic or medication, there is the problem of how to fix or anchor the catheter and associated filter to the patient. It must be avoided that the catheter is accidentally pulled out of the patient during moving of the patient. Also, the securing of the catheter and the filter by adhering to a surface of the body of the patient can result in certain cases that the supply of the anesthetic is pinched off. In addition, in the case of this inflexible fixing there is the danger that during movement of the patient the catheter can be pulled out, which risk is particularly large.

DE 297 20 182 U1 describes a foamed bandage, which can be adhered to the skin of the patient, with a perpendicularly oriented pin, upon which the filter can be freely rotatably mounted. The filter, which is thus anchored via the bandage locally to the surface of the body of the patient and is connected via the catheter with the patient, can follow the movement of the patient during rotation of the patient and catheter. Nevertheless here, also the catheter must be secured to the patient by an adhesive strip.

From DE 1 954 956 a device for securing a catheter is known, in which the catheter is clamped into a channel of a mounting block, wherein the channel has a diameter which corresponds to the outer diameter of the catheter. The effect of this device for securing a catheter corresponds essentially to that of an adhesive strip,.since a defined point of the catheter is fixed to the body of the patient.

SUMMARY OF THE INVENTION

The task of the invention is comprised therein, of providing a device, which reliably anchors catheter and filter to the patient, without substantially interfering with the freedom of movement of the patient.

The task is solved by a device for anchoring a filter and a catheter according to patent claim 1.

Advantageous embodiments and further developments of the invention are set forth in the dependent claims.

The inventive device for anchoring a filter and a catheter includes an adhesive bandage, a securing element for anchoring the catheter, and a carrier element for mounting the filter, wherein either the securing element or the carrier element is applied to the adhesive bandage, and wherein the securing element includes a first coupling element, which is releasably connectable with a second coupling element provided on the carrier element. Therewith it becomes possible with one device to simultaneously anchor the catheter and filter on the patient.

The securing element preferably includes openings, of which the axes are approximately parallel to the plane of the securing element. These openings receive the catheter, whereby it is anchored to the body of the patient.

In a preferred further embodiment of the invention the openings are designed in such a manner that the diameter of the openings is somewhat larger than the diameter of the catheter. The catheter is thus located or positioned by the securing element, but can however be slid freely back and forth in the openings of the securing element. Therewith, the catheter is anchored to the patient, however axially moveable to the extent that it can follow any movement of the patient and thus there is no danger that the catheter can be pulled out by a movement of the patient.

Preferably the securing element includes gaps or slits, which are open on the surface of the securing element and widen on the base toward the openings. Instead of having to thread the catheter through the openings and subsequently introduce it into the patient or connecting it to the filter, it is thereby possible, to press-in the catheter through the gap or slit in the opening of the securing element after it has already been introduced into the patient and connected to the filter.

Preferably the breadth of the gap is slightly smaller than the diameter of the catheter. In this way the catheter is trapped in the opening and therewith anchored to the disc, can however continue to be freely moved axially back and forth in the openings of the securing element.

In an advantageous further development of the invention the openings in the bars provided on the surface of the securing element are oriented parallel to the plane of the securing element. The openings are therewith particularly easily accessible. Preferably, the bars are provided in the shape of a right-angled cross.

The catheter can be introduced between two openings of the bar with some surplus such as with a loop. During movement of the patient the part of the catheter distant from the patient slides in the opening, whereby the loop increases or as the case may be becomes smaller. The part of the catheter close to the patient is however held securely in the securing element, so that the catheter cannot be pulled out.

Preferably one of the two coupling elements is in the form of a pin, while the other of the two coupling elements is in the form of an opening, into which the pin can be introduced. Preferably the pin and the opening are in the form of engaging elements or form fitting or self-locking elements, which makes possible a particularly simple connection of the securing element and the carrier element.

Preferably the pin and the opening are in the form of a polygon, for example a symmetric hexagon or octagon. The filter can therewith be anchored in multiple positions in relation to the securing element, depending upon how the catheter is running relative to the patient.

Preferably the filter is releaseably secured to the carrier element. Therewith a particularly simple changing out of the filter is made possible, while the device for anchoring of catheter and filter to the body of the patient remains.

Preferably the filter is securable to the carrier element via a clamping or lock engagement function.

BRIEF DESCRIPTION OF THE DRAWING

One embodiment of the invention is described in greater detail in the following on the basis of the figure. There is shown:

FIG. 1 a top view on the bandage with a securing element;

FIG. 2 a side view of the bandage with the securing element;

FIG. 3 an axial section of the securing element;

FIG. 4 a sectional enlargement of FIG. 3,

FIG. 5 a top view on the carrier element,

FIG. 6 a side view of the carrier element,

FIG. 7 an axial section of the carrier element,

FIG. 8 an axial section through the illustrated embodiment of the invention comprised of bandage, securing element and carrier element, FIG. 9 a sectional enlargement of FIG. 8, FIG. 10 an axial section through a illustrated embodiment of the invention comprised of bandage, securing element and carrier element with introduced filter and catheter, and FIG. 11 a top view on the embodiment of FIG. 10.

DETAILED DESCRIPTION OF THE INVENTION

FIG. 1 shows one embodiment of the inventive device for anchoring catheters and filters comprised of an adhesive bandage 10 and a securing element 20 secured centrally thereupon for example with an adhesive strip. The adhesive bandage 10 has a self-adhesive layer on the back side, with which the adhesive bandage 10 can be secured to the body of a patient.

The securing element 20 is comprised of a round plastic disc, upon which are formed two bars 22 running radially and perpendicular to each other. The bars 22 have through-going openings 24 oriented parallel to the plane of the securing element 20 and in the tangential direction. Each radial bar 22 has three openings 24 equally spaced radially. The diameter of the openings 24 is somewhat larger than the diameter of the catheter to be secured, in order to guarantee a free axial moveability of the catheter in the opening 24.

From the upper side of the bar 22 a narrow gap or slit 26 leads into the respective openings 24, via which the catheter can be pressed into the openings 24 (see FIG. 2). The diameter of the catheter is therein slightly larger than the breadth of the gap 26, so that the catheter after introduction into the opening 24 cannot be removed without application of force out of the opening 24. The catheter is therewith anchored via the securing element 20, can however be slid along the axis of the opening 24.

The securing element 20 exhibits an axial opening 28 centrally in the crossing point of the two bars 22, in which a carrier element 30 can be seated via a pin or plug 32 introduced axially into the carrier element 30. The axial opening 28 exhibits, proceeding from the surface of the bars 22, a conically narrowing segment 28a, which transitions, via an inward directed flange 29 running about the inside of the axial opening 28, into a cylindrical section 28b (see FIGS. 3 and 4). Beginning at the bottom side of the carrier element 30, the pin or plug 32 is first cylindrical, and transitions to a spring or elastic segment with slightly larger diameter and having a cross-wise slit-like cut (see FIGS. 6 and 7). If the carrier element 30 is seated on the securing element 20, the springy segment engages with its slightly larger diameter of the pin 32 behind the inner band or flange or shoulder 29 (see FIGS. 8 and 9). The carrier element 30 is held securely yet releaseably on the securing element 20 via this coupling connection.

The cross section of the axial opening 28 and the pin or plug 32 are non-circular and exhibit for example the shape of a octagon. The carrier element 30 can thus be engaged in eight different angular positions relative to the securing element 20, wherein it is held secure against rotation in each position.

The carrier element 30 is comprised of a round disc of plastic, of which the circumference is flattened by two secant lines running parallel to each other (see FIG. 5). An edge 36 is formed perpendicular to the plane of the carrier element 30 at the two remaining circumference segments, which exhibits on its upper edge an inward projecting circumferential spring 34, which engages in a corresponding groove of a not shown filter to be inserted.

FIGS. 10 and 11 show the use of the inventive device for anchoring of a catheter 40 and a filter 50. In order to secure the catheter 40 and the filter 50 to a patient by means of the inventive device, first the adhesive bandage 10 is adhered to the skin of the patient by means of the adhesive layer at the bottom side of the adhesive bandage 10. The one end 40a of the catheter 40 is applied to the patient. Subsequently the catheter 40 is introduced into at least one opening 24 of the securing element 20, and preferably in at least two with formation of a loop or undulation. The proximal end 40b of the catheter 40 is connected via a connecting element 42 to an appropriate connecting element 52 provided on the filter 50. Thereupon the carrier element 30 is seated with the pin or plug 32 in the axial opening 28 of the securing element 20 and the filter 50 is clamped on the carrier element 30. By a connection 55 provided on the filter 50, the anesthetic or medication can now be applied.

It is of course conceivable that also the carrier element can be applied to the adhesive bandage. Then, the securing element is engaged upon the carrier element with clamped-in filter by means of a coupling unit, upon which the catheter is anchorable.

REFERENCE NUMBER LIST 10 adhesive bandage
20 securing element
22 bar
24 opening
26 gap
28 opening
28a conical section
28b cylindrical section
29 inner flange
30 carrier element
32 pin
34 spring
36 edge
40 catheter
40a end of the catheter
40b end of the catheter
42 connecting element
50 filter
52 connecting element
55 connection

The invention claimed is:

1. A device for anchoring a filter (50) and a catheter (40), comprising:
    an adhesive bandage (10),
    a securing element (20) for anchoring the catheter (40), wherein the securing element has a surface having a plane and
    a carrier element (30) for anchoring the filter (50),
    wherein either the securing element (20) or the carrier element (30) is applied to the adhesive bandage (10),
    wherein the securing element (20) includes bars (22) extending from the surface, wherein each of said bars (22) extends along a longitudinal axis, wherein openings (24), each having an axis substantially perpendicular to the longitudinal axis of the bar and substantially parallel to the plane of the securing element (20), are provided in the bars, and
    wherein the securing element (20) includes a first coupling element, which is releasably connectable with a second coupling element provided on the carrier element (30).

2. The device according to claim 1, wherein the width of the openings (24) is larger than the diameter of the catheter (40).

3. The device according to claim 2, wherein the securing element (20) includes gaps (26) having a breadth, which lead from the surface of the securing element (20) into the openings (24).

4. The device according to claim 3, wherein the breadth of the gaps (26) is slightly smaller than the diameter of the catheter (40).

5. The device according to claim 1, wherein the bars (22) are arranged in the shape of a cross.

6. The device according to claim 1, wherein the first coupling element or the second coupling element is a plug (32), wherein the other coupling element is in the form of an opening (28), in which the plug (32) is introducible.

7. The device according to claim 6, wherein the plug (32) and the opening (28) are self-locking elements.

8. The device according to claim 6, wherein the plug (32) and the openings (28) in cross section are corresponding polygons.

9. The device according to claim 1, wherein the filter (50) is releasably secured upon the carrier element (30).

10. The device according to claim 9, wherein the filter (50) is securable upon the carrier element (30) via a clamping or engaging function.

11. A device for anchoring a filter (50) and a catheter (40), comprising:
   an adhesive bandage (10),
   a securing element (20) for anchoring the catheter (40) having a plane; and
   a carrier element (30) for anchoring the filter (50), wherein the carrier element is in direct contact with the securing element;
   wherein either the securing element (20) or the carrier element (30) is applied to the adhesive bandage (10),
   wherein the securing element (20) includes a first coupling element that interconnects with a second coupling element provided on the carrier element (30), and
   wherein the securing element (20) includes bars (22), wherein each of said bars (22) extends along a longitudinal axis, wherein openings (24), each having an axis substantially perpendicular to the longitudinal axis of the bar and substantially parallel to the plane of the securing element (20), are provided in the bars.

12. A device for anchoring a filter (50) and a catheter (40), comprising:
   an adhesive bandage (10),
   a securing element (20) for anchoring the catheter (40), the securing element having a plane; and
   a carrier element (30) for anchoring the filter (50),
   wherein the carrier element and the securing element are located in different planes;
   wherein either the securing element (20) or the carrier element (30) is applied to the adhesive bandage (10),
   wherein the securing element (20) includes a first coupling element that interconnects with a second coupling element provided on the carrier element (30), and
   wherein the securing element (20) includes bars (22), wherein each of said bars (22) extends along a longitudinal axis, wherein openings (24), each having an axis substantially perpendicular to the longitudinal axis of the bar and substantially parallel to the plane of the securing element (20), are provided in the bars.

* * * * *

UNITED STATES PATENT AND TRADEMARK OFFICE
CERTIFICATE OF CORRECTION

PATENT NO. : 7,074,208 B2
APPLICATION NO. : 10/716281
DATED : July 11, 2006
INVENTOR(S) : Pajunk et al.

Page 1 of 1

It is certified that error appears in the above-identified patent and that said Letters Patent is hereby corrected as shown below:

On Title Page Item (30)
add field (30)
    --Foreign Application Priority Data
Nov. 19, 2002 (DE) ............... 202 17 920.6--

Signed and Sealed this

Second Day of January, 2007

JON W. DUDAS
*Director of the United States Patent and Trademark Office*